(12) United States Patent
Krill et al.

(10) Patent No.: US 6,469,215 B1
(45) Date of Patent: Oct. 22, 2002

(54) PROCESS FOR THE PRODUCTION OF AN INTERMEDIATE MIXTURE OF β-ISOPHORONE EPOXIDE AND ITS ISOMER 4-HYDROXYISOPHORONE (HIP)

(75) Inventors: Steffen Krill, Speyer; Klaus Huthmacher, Gelnhausen, both of (DE); Sylvain Perrin, Gueugnon (FR)

(73) Assignee: Degussa AG (DE)

( * ) Notice: Subject to any disclaimer, the term of this patent is extended or adjusted under 35 U.S.C. 154(b) by 0 days.

(21) Appl. No.: 10/084,157

(22) Filed: Feb. 28, 2002

Related U.S. Application Data

(62) Division of application No. 09/850,156, filed on May 8, 2001.

(30) Foreign Application Priority Data

May 17, 2000 (DE) .......................................... 100 24 264

(51) Int. Cl.$^7$ ...................... C07C 45/67; C07D 315/00; C07D 309/00
(52) U.S. Cl. ...................... 568/341; 568/342; 568/343; 568/346; 549/425
(58) Field of Search ............................... 568/341, 342, 568/343, 346; 549/425

(56) References Cited

U.S. PATENT DOCUMENTS

| 4,046,813 A | 9/1977 | Brenner |
| 4,898,984 A | 2/1990 | Bellut |
| 5,874,632 A | 2/1999 | Hahn et al. |

FOREIGN PATENT DOCUMENTS

| DE | 3806835 A1 | 9/1989 |
| GB | 791953 | 3/1958 |

OTHER PUBLICATIONS

Copy of PCT International Search Report for counterpart application PCT/EP01/04815, dated Sep. 26, 2001.

R. Hutter, et al., "Control of Acidity and Selectivity of Titania–Silica Aerogel for the Epoxidation of β–isophorone," *Journal of Molecular Catalysis A:Chemical* 183 (1999), pp. 241–247

*Chemical Abstracts*, vol. 76, No. 23, Jun. 5, 1972, Columbus, Ohio, Abstract No. XP–002177009.

Database Crossfire Reactions Online! Beilstein; Reaction ID 4392631, Abstract No. XP–002177010 (1996).

*Primary Examiner*—Sreeni Padmanabhan
*Assistant Examiner*—Sikarl A. Witherspoon
(74) *Attorney, Agent, or Firm*—Smith, Gambrell & Russell LLP

(57) ABSTRACT

A process for the production of an intermediate mixture of β-isophorone epoxide and its isomer 4-hydroxyisophorone (HIP), comprising reacting β-isophorone with an organic percarboxylic acid, in the form of its non-aqueous solution, in an inert solvent.

5 Claims, No Drawings

PROCESS FOR THE PRODUCTION OF AN INTERMEDIATE MIXTURE OF β-ISOPHORONE EPOXIDE AND ITS ISOMER 4-HYDROXYISOPHORONE (HIP)

The present application is a divisional of Ser. No. 09/850,156, filed May 8, 2001, which prior application is incorporated herein by reference.

The present invention relates to a process for the production of dihydroketoisophorone (DH-KIP; 2,2,6-trimethylcyclohexane-1,4-dione) by epoxidation of β-isophorone with a percarboxylic acid solution in an inert, non-water-soluble solvent, which is, at the same time, the solvent used for epoxidation: of β-isophorone (β-IP) to β-isophorone epoxide (β-IPO) and subsequent isomerization to 4-hydroxyisophorone (HIP) and the product DH-KIP. In particular, an industrially advantageous process is provided, in which the reaction sequence: epoxidation, ring opening of the epoxide to HIP and isomerization of HIP to the product takes place in a pH range which allows the entire synthesis sequence to be carried selectively without the need for frequent changes from acid to basic condition.

In particular, an advantageous process is described, in which all reactions can be carried out one after the other in one reaction unit, without the need for intermediate isolation of discharged intermediates.

The DH-KIP obtained from this process can be converted directly to trimethylhydroquinonediacetate (TMHQ-DA) by oxidative aromatization. Trimethylhydroquinonediacetate is a central educt of vitamin E acetate synthesis. DH-KIP is also an important component for various carotinoid syntheses. In addition to its uses in the human sphere, vitamin E acetate is used in the form of special formulations as an additive for animal feed.

3,5,5-trimethyl-4-hydroxy-cyclohex-2-en-1-one (HIP) is described in the literature as a flavoring and aromatizing substance (JP-81 35 990; CH 549 961; DE 22 02 066). Its use as a food flavoring is also known (CH 549 956; M. Ishikara et al., J.Org. Chem. 1986, 51, 491 et seq.). HIP also has a variety of applications as a synthetic component for natural products and various pharmaceuticals (N. S. Zarghami et al., Phytochemistry 1971, 10, 2755 et seq.; J. N. Marx and F. Sondheimer, Tetrahedron Lett., Suppl. No. 8, Pt 1, 1–7, 1966). In particular β-IPO is an important intermediate for the synthesis of 2,6,6-trimethylcyclohexane-1,4-dione and thus for vitamin E. The conventional synthesis sequence is as follows:

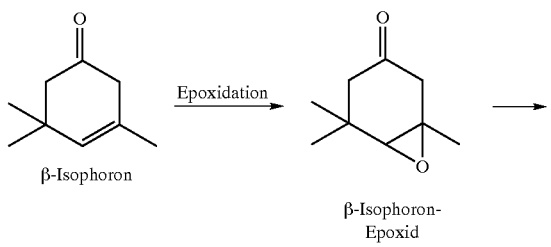

β-Isophoron

β-Isophoron-Epoxid

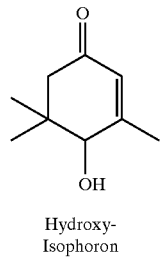

Hydroxy-Isophoron

The known processes for the production of β-IPO produce only unsatisfactory yields. It was found that oxidation of β-isophorone normally proceeds to 4-oxo-isophorone, hydroxyisophorone being formed in concentrations of 1–50%, depending on the oxidizing agent used. The formation of hydroxyisophorone appears, according to the processes described, to be a secondary reaction. If the course of the reaction is followed, it becomes clear that hydroxyisophorone is not the intermediate product of 4-oxo-isophorone, as HIP is virtually inert under the oxidation conditions.

The epoxidation of β-isophorone originates with Isler et.al. (Helv. Chim. Acta 39, 1956, 2041 et seq.), who carry out epoxidation with peracetic acid as the oxidizing agent in acetic acid as the solvent and, after changing the pH value to 8–9 with aqueous sodium hydroxide solution, isolate only unsatisfactory yields of HIP. The need to basify with dilute sodium hydroxide solution the solution first obtained, which contains β-IPO, for the production of HIP; gives rise to a stoichiometric salt load (formation of sodium acetate) and prevents recycling of the organic acid. No details are given of the isomerization of β-IP to alpha-isophorone which occurs as a secondary reaction. The yields of HIP from β-IP according to this publication, amount to only about 60%, due to the formation of alpha-IP and the non-selective ring opening of β-IPO to HIP.

The same procedure is described in British patent 791 953, although no details of yields and the formation of by-products are given here. U.S. Pat. No. 2,857,423 by the same authors gives an equally incomplete description of the production of DH-KIP. According to these publications DH-KIP is formed either from HIP by acid catalysis, HIP being produced in a separate reaction and isolated, or from ketoisophorone by partial hydrogenation of the double bond.

Zarghami et al. also (Phytochemistry 10, 1971, 2755 et seq.) do not disclose yields of β-IP epoxide from their reaction with peracetic acid. Tetrahedron Lett. Suppl. No. 8, Pt. 1, 1966, 1–7 gives a further description of the epoxidation of β-isophorone. Organic solvents such as chloroform, using meta-chlorobenzoic acid as the oxidizing agent, are described, m-chlorobenzoic acid being precipitated out from the solution after completion of the redox reaction and a product profile being produced which consists of β-IP epoxide and HIP in a ratio of 1:1, and alpha-isophorone. It is obvious that, according to this process, neither the undesirable re-isomerization to alpha-IP nor the consecutive reaction to HIP can be suppressed. After hydrolysis at a basic pH, 87% HIP is isolated. This procedure is unsatisfactory as the pH environment must be changed several times to produce HIP, which entails a significant salt load and produces only moderate yields.

All of these processes have in common that they produce unsatisfactory yields of β-isophorone epoxide, due to the non-selective reaction process or unsuitable oxidizing agent, or to the presence of water in the reaction medium, which both catalyzes the reverse reaction of β-isophorone and destabilizes the epoxide. The formation of the diol can also be detected from the β-IP epoxide as a result of the accumulation of water.

A further reaction, observed when the reaction is not sufficiently controlled, is the epoxidation of alpha-IP (which is formed in "situ" from β-IP by isomerization) to alpha-IP epoxide, and its consecutive reaction of isomerization to 2-hydroxyisophorone. These principal secondary reactions are observed also in epoxidation with other substrates, the diols and hydroxyesters being obtained in particular (see W. M. Weigert, Wasserstoffperoxid und seine Derivate [Hydrogen peroxide and its derivatives], Hüthig Verlag Heidelberg 1978, page 79 et seq.).

The following diagram shows the possible secondary and consecutive reactions of β-IP epoxidation:

such as bases, being necessary to achieve higher selectivities, partly in order to suppress the formation of HIP. Although this process has achieved the best epoxide selectivities hitherto, it is not advantageous to use alkylhydroperoxides, which are spent stoichiometrically, for an industrial process. It is also undesirable to use a heterogeneous contact, which is costly to prepare.

DP 38 06 835 describes the oxidation of β-IP to HIP by reaction with aqueous hydrogen peroxide in the presence of formic acid. β-IP epoxide is discharged as an intermediate, but a re-isomerization rate in the range 20–35% make the process unattractive from an industrial point of view.

No satisfactory process is described, in particular for the rearrangement of β-isophorone epoxide or a mixture of the β-IPO first obtained by epoxidation and hydroxyisophorone. The process suggested in British patent 791 953 for the rearrangement of HIP to DH-KIP is laborious, as HIP must

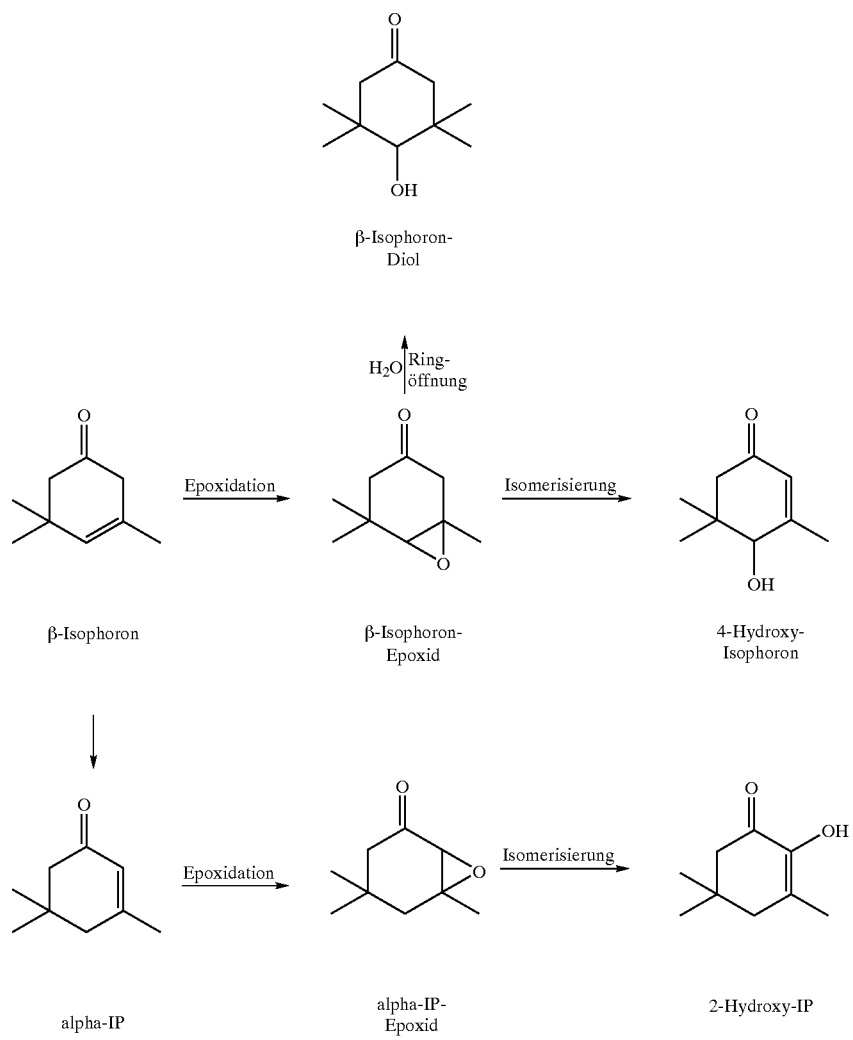

The epoxidation of β-isophorone in the presence of anhydrous peroxidation reagents such as alkylhydroperoxides is also described (Hutter, Baiker et al., Journal Mol. Cat. 172, 427–435, 1997). A heterogenous contact $SiO_2$—$TiO_2$ mixed oxide activates the peroxide, expensive pre-treatment of the catalyst, or the addition of further auxiliary substances first be produced from β-IPO by basic hydrolysis in a separate process step. The consecutive reaction with strong acids, as described in Isler et al., Helv. Chem. Acta, (1956), No. 237 page 2041, is as laborious as it is non-selective, as HIP must be provided as a pure substance and rearrangement to DH-KIP in the presence of strong acids entails the formation of trimethylphenols as by-products. A reaction time of 20 h is also a substantial disadvantage of this process.

Hitherto, there has been no known process which allows DH-KIP to be produced using inexpensive, industrially efficient and accessible oxidizing agents and high product selectivity, in particular from a readily available mixture of β-isophorone epoxide and hydroxyisophorone. This is the basis of the objects to be achieved by the invention.

An object of the present invention is to produce dihydroketoisophorone (DH-KIP) from β-isophorone with high selectivity and yield, suppressing in particular the re-isomerization of the educt to alpha-isophorone, to avoid having to separate alpha-IP from the product solution by expensive means and having to change the environment from acid (environment for epoxidation with organic percarboxylic acids) to basic (prior art for the production of HIP from β-IPO) and back to acid (prior art for rearrangement of HIP to DH-KIP). Furthermore a process is to be provided, which makes it possible to convert the mixture of β-IPO and HIP obtained "in situ" directly to DH-KIP and to reduce considerably the long reaction times in the prior art.

A further object of the invention is to provide a process for converting β-isophorone epoxide to DH-KIP, β-isophorone epoxide with its isomer hydroxyisophorone being produced from β-isophorone in a first reaction step by reaction with an organic peracid.

SUMMARY OF THE INVENTION

The above and other objects can be achieved in that β-isophorone is brought into contact at moderate temperatures with an organic percarboxylic acid dissolved in an organic solvent, the organic solvent being at the same time the extracting agent used to extract the organic peracid as it is produced, and the β-IPO thus obtained together with its isomer hydroxyisophorone which is present as a by-product in a concentration of 0.1–80 mol % (in relation to β-IPO) is isomerized to DH-KIP by thermal isomerization in the presence of the organic carboxylic acid or by reaction in the presence of a salt as catalyst.

According to the process, inexpensive raw materials such as aqueous hydrogen peroxide, organic carboxylic acids and a solvent on the one hand and, in the simplest case, alkali-or earth alkali salts on the other, can be used, and as only the educt substrate β-isophorone and hydrogen peroxide are spent during the epoxidation process, the majority of the other raw materials can be recycled. The catalysts used for the isomerization of β-IPO/HIP solutions can also be recycled and in this sense are not specific consumption materials.

The first aspect of the invention relates to a new process for the production of dihydroketoisophorone by epoxidation of β-isophorone (β-IP) by reaction with a peracid in the form of its solution in a suitable solvent in the liquid phase, which is stable under reaction conditions, thus substantially avoiding separation into two phases which can occur if there is a high concentration of water in the reaction mixture, and obtaining a mixture of organic carboxylic acid, extracting agent (=solvent), β-isophorone epoxide with hydroxyisophorone as the product solution. In the simplest form of the process according to the invention, the solvent used for oxidation is also the agent for extracting the corresponding peracid as it is produced from an aqueous hydrogen peroxide solution, carboxylic acid and sulfuric acid.

The second aspect of the process according to the invention relates to the rearrangement of the β-IPO formed in "situ", which, depending on the production process, may contain 0.1–80 mol % hydroxyisophorone, by direct thermal isomerization of the solution obtained from epoxidation or isomerization of the epoxidation solution obtained directly from the reaction in the presence of an additional catalyst salt, in the simplest case an alkali- or earth alkali salt or other suitable isomerization catalysts, or by isomerization of an epoxidation solution, the majority of which at least is first released from the carboxylic acid by extraction or distillation.

To achieve high selectivity, the reaction is carried out in two temperature stages.

DETAILED DESCRIPTION OF INVENTION

In particular, the present invention is a process for the production of dihydroketoisophorone (2,2,6-trimethylcyclohexane-1,4-dione)

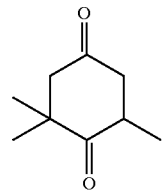

by reacting -isophorone (3,5,5-trimethylcyclohex-3-en-1-one)

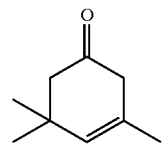

with an organic percarboxylic acid in the form of its non-aqueous solution in an inert organic solvent at a temperature of 0° C. to 300° C., the percarboxylic acid used as the oxidizing agent being formed in a pre-determined equilibrium and absorbed or extracted with the solvent used for oxidation, characterized in that, the mixture of the β-isophorone epoxide formed first

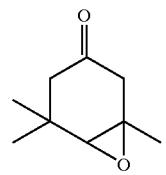

and the isomer 4-hydroxyisophorone (HIP),

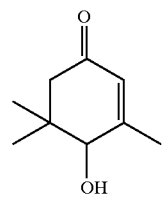

is isomerized "in situ" thermally or in the presence of an acid catalyst or in the presence of a salt.

Epoxidation of β-IP takes place at temperatures of –50° C. to 100° C. and in a preferred embodiment at temperatures of 0° C. to 60° C. The reaction times in this temperature range are fast enough when used as an industrial process, to achieve complete conversion of β-isophorone within 0.5–5 h. For safety reasons, a method can also be chosen which uses an excess of β-isophorone in relation to the percarboxylic acid used, but the stoichiometric consumption of percarboxylic acid at moderate temperatures is fast enough, even with this variant.

Although the reaction can also be carried out at higher temperatures, this measure increases the proportion of hydroxyisophorone. High product selectivities can be achieved at lower temperatures, but the reaction speed is reduced and a cooling brine must be used.

Isomerization of the intermediate product mixture from epoxidation (consisting of β-IPO and HIP) takes place at temperatures of 0° C.–300° C., and depends substantially on the desired reaction time, the catalyst used and its concentration. In a preferred embodiment the working temperature is 20° C. to 200° C. Reaction times in this temperature range are fast enough when used as an industrial process to achieve complete conversion of β-IPO/HIP to DH-KIP within 0.5–3 h.

In a further embodiment of the process according to the invention, epoxidation and isomerization are carried out simultaneously in one temperature range, the presence of the isomerization salt during epoxidation being a characteristic of this embodiment. According to a simple variant of this embodiment, β-IP is provided with or without solvent, in the presence of the salt catalyst, e.g. $MgBr_2$, and percarboxylic acid is added to the organic solvent at temperatures of 20° C.–150° C.

The ratio of β-isophorone to the peracid used as the oxidizing agent is not critical for product selectivity and, depending on the method used, can be selected in a molar ratio of β-IP: percarboxylic acid =10:1 to 1:10. A preferred molar ratio of the components is in the range 2:1 to 1:2. In view of the potential risks of working with peracids it is possible to use slightly less of the epoxidizing agent in relation to the β-isophorone, so that when the reaction is complete, the peracid has been converted, forming the corresponding carboxylic acid and only a slight concentration of excess β-isophorone is present. The unconverted β-isophorone can either be re-used as it is for preparation or, after isomerization to alpha-IP, can be fed back into the β-IP production process.

The concentration of peracid in the extracting agent or the solvent used for oxidation can be 1 wt.-% to 50 wt.-%, the preferred range on safety grounds being 5 wt.-%–30 wt.-%. The maximum concentration range of peracid in the organic solvent to be selected must in particular depend on the choice of peracid used, the solvent and the oxidation temperature.

A plurality of commercial organic solvents can be used as the oxidizing solvent or as the agent for extracting the peracid.

The β-isophorone epoxide obtained at the end of the reaction can be further converted under suitable conditions directly after isolation. In particular, after isolation, β-IPO can be converted by known processes to hydroxyisophorone or to 2,2,6-trimethyl-cyclohexane-1,4-dione (DH-KIP= dihydroketoisophorone). The isolation of β-IPO can be avoided in the process according to the invention, by converting the organic mixture of β-IPO and HIP directly in the presence of a suitable catalyst, in particular a Lewis acid or various salt catalysts.

The organic carboxylic acid used for the present process is preferably an aliphatic, alicyclic, aromatic carboxylic acid having 1–20 hydrocarbon atoms, wherein the hydrocarbon group may have one or more functional groups. Formic acid, acetic acid, propionic acid, butyric acid, valeric acid and higher homologues are-preferred as percarboxylic acid-forming carboxylic acids. Particularly preferred are non-aqueous solutions of performic acid, peracetic acid, perpropionic acid and homologous peracid compounds having 1–20 hydrocarbon atoms. Examples of the branched derivatives which may be used are isobutyric acid, pivalic acid and neopentyl carboxylic acid. Examples of aromatic, substituted and unsubstituted percarboxylic acid-forming carboxylic acids are benzoic acid, m-chloro- and p-nitrobenzoic acid, and also monoterephthalic acid. Halogenated derivatives such as for example trihalogenated acetic acid (trichloro-, trifluoroacetic acid) are also suitable.

The production of the peracid from the corresponding carboxylic acid is known per se. It is explained in one embodiment by the example of the formation of peracetic acid. Acetic acid is normally reacted with aqueous hydrogen peroxide in the presence of an acid catalyst (in the case of carboxylic acids activated by corresponding substituents which have sufficient acidity, there is no need to supplement with additional catalyst acids. Formic acid also forms performic acid "in situ" in the presence of hydrogen peroxide without the need for the addition of a mostly mineral catalyst acid).

Normally sulfuric acid is used as the catalyst acid. In the present invention, the peracid used as an oxidizing agent is preferably formed in a pre-determined equilibrium reaction from the corresponding carboxylic acid, an aqueous hydrogen peroxide solution and sulfuric acid and absorbed and extracted with the solvent used for oxidation and isomerization. Mixing carboxylic acid/aqueous hydrogen peroxide/sulfuric acid produces more or less pure aqueous solutions of the peracetic acid and, after establishing equilibrium, a so-called equilibrium peracetic acid of the following composition (Ullmans Encyclopaedia of Technical Chemistry, 3rd edition, vol. 13, p. 254):

peracetic acid: approx. 40–42% acetic acid: approx. 37–40% water: approx. 10–14%

$H_2O_2$: approx. 4–6% sulfuric acid: approx. 0.5–1%

Very clean aqueous solutions are obtained if, as well as the catalyst acid and water, a mol quotient $H_2O_2$: peracid of >1 is added and after equilibrium has been established the peracid is removed from the top of a distillation column as an azeotrope with water at reduced pressure. According to DE 11 65 576, anhydrous solutions of the peracid in an organic medium can be produced from these solutions. The anhydrous or water-depleted solution of the peracid in an organic medium can also be produced from the reaction mixture $H_2O_2$- catalyst acid - carboxylic acid by azeotropic distillation of the water with a suitable solvent (see Ullmans Encyclopaedia of Technical Chemistry, suppl. volume, 3rd edition, p. 181). A further method which, with regard to the safety risks associated with handling these solutions, can be classified as comparatively safe, is to extract the peracid directly from the aqueous solution containing the percarboxylic acid, using a suitable extracting agent.

It has been found that the isomerization can also be catalyzed by the carboxylic acid formed from reduction of percarboxylic acid.

Suitable extracting agents for the purposes of the invention are described in DE 21 45 603, including aliphatic, cycloaliphatic, aromatic solvents, but halogenated derivatives of compounds from these classes of substances are also suitable, in particular chlorinated hydrocarbons such as methylene chloride and chloroform. The hydrogen peroxide solutions used may have an $H_{2O2}$ content of 10–90 wt.-%, commercial aqueous peroxide solutions with a content of 30–85 wt.-% being used in particular, and preferably a solution with a content of 45–70 wt.-%.

An equally suitable solution for the epoxidation of β-isophorone can be produced from ripened solutions of percarboxylic acids by extraction with phosphoric acid esters, in particular trialkylphosphates according to U.S. Pat. No. 3,829,216. Here absorption is first carried out with the stated phosphoric acid esters and then the 10–80 wt.-% peracid solutions are desorbed with an alkyl ester, to form, finally, solutions of the peracid in an alkyl ester.

In a preferred embodiment of the process according to the invention, the water-depleted solution of the organic percarboxylic acid is produced according to U.S. Pat. No. 4,904, 821. This patent describes the production of a percarboxylic acid solution in alkyl phosphates, by placing $H_2O_2$ (30–35 wt.-% aqueous solution) and acetic acid in a molar ratio of 1 to 2:1 in the bottom of a distillation column, setting the quantity of sulfuric acid to 20–30 wt.-% in relation to the volume of the total solution and removing a mixture of acetic acid, peracetic acid and water from the top at temperatures of 55° C. to 70° C. at reduced pressure. The vapors are absorbed in a suitable phosphoric acid trialkylester while non-absorbed water can be removed from the top of this absorption column.

The solutions of the percarboxylic acid along with the corresponding carboxylic acid in the phosphoric acid ester are then used directly for epoxidation, or the solutions are converted to another conventional solvent by desorption.

The contents of percarboxylic acid solutions in the solvent or in the extracting agent are no 1–50 wt.-%, aiming preferably for a dilution of <30 wt.-%, in order to ensure safe handling.

The process according to the invention can be carried out as described in the presence of organic solvents which are inert under reaction conditions. The concentration of the reagent in the solvent has little influence on the product profile of the reaction and is substantially dependent on safety aspects. A solvent-free method can also be used, in which case β-isophorone is brought directly into contact with the solution containing the peracid, if it can be ensured that the water concentration of the solution containing the peracid is low enough to suppress substantially both re-isomerization to alpha-IP and consecutive reaction of the epoxide to HIP. The water concentration of the organic solution of percarboxylic acid used should normally be lower than 5 wt.-%, and is preferably 0.01 to 2 wt.-%.

The solvents used must normally be stable in the presence of peracids. A further selection criterion is that they should be easy to separate by distillation from the carboxylic acid used and from the product.

If epoxidation is carried out in the presence of organic solvents, it is advantageous to use aliphatic and cyclic esters, for example acetic acid methylester, acetic acid ethylester, acetic acid propyl ester, butyl acetate, isobutyl acetate, gamma butyrolactone, ethylene carbonate, derivatives and homologues thereof, aliphatic, alicyclic and aromatic hydrocarbons, for example pentane, hexane, heptane, octane and other homologues, benzene, toluene and xylene. Ketones such as for example acetone, methyl ethyl ketone, diethyl ketone and isophorone are also suitable as solvents within the scope of the invention. Aliphatic, aromatic or mixed ethers such as diethyl ether, methyl tertiarybutyl ether can also be used, although their use is limited for safety reasons. Suitable organic phosphoric acid esters are those of which the substituents contain 3–30 -hydrocarbons, for example phosphoric acid triester, the substituents of which can be of an aliphatic, alicyclic or aromatic nature. Examples of these are tricycylohexylphosphate, triphenylphosphate tricresylphosphate, diphenylcresylphosphate, triethylphosphate, tributyl-phosphate, trioctylphosphate and other derivatives and homologues.

Other suitable classes of solvent are halogenated hydrocarbons. Mixtures of these solvents can also be used.

The rearrangement of the mixture of β-isophorone epoxide and hydroxyisophorone obtained "in situ" which, depending on the parameters set for epoxidation, has a concentration of 0.1–80 mol % in relation to β-IPO, can in principle be carried out by various methods.

As a one-pot process from β-IP to DH-KIP without intermediate isolation of β-IPO/HIP solutions: According to this variant epoxidation of β-IP is carried out in the presence of an isomerization catalyst, which catalyzes the conversion of both β-IPO and HIP to DH-KIP.

According to the indirect process variant, epoxidation is carried out first and, after separation from the carboxylic acid, the β-IPO/HIP product mixture is then converted to DH-KIP by the addition of isomerization catalysts.

The main catalysts for isomerization of β-IPO and HIP to DH-KIP are Brönstedt- or Lewis acids, but various salts, in particular alkali- and earth alkali salts, which have no exceptional acidity, can be used.

The Brönstedt acids which can be used according to the invention as isomerization catalysts, are mainly protonic acids with a pKA value of less than 10. This covers relatively mild catalyst acids in a pKA range of pKA=3–10 such as carbonic acid, ammonium or pyridinium salts, boric acid or common organic carboxylic acids (substituted or unsubstituted) such as acetic acid, propionic acid or chloroacetic acid and similar compounds. Di- or tricarboxylic acids such as oxalic acid, malonic acid, adipic acid and higher homologues or citric acid and related compounds can be used as carboxylic acids.

Other more active isomerization catalysts are protonic acids with a pKA<3 of the group sulfuric acid, hydrohalic acid (HCl, HBr, HI), fluoroboric acid, aromatic sulfonic acids such as p-toluene sulfonic acid or benzene sulfonic acid, trifluoroacetic acid, chloroacetic acid or corresponding aromatic carboxylic acids, which are activated by electron-attracting groupings such as picric acid, nitroterephthalic acid and derivatives.

Active Lewis acids used as isomerization catalysts according to the invention are, for example, compounds of the aluminum halogenide group ($AlCl_3$, $AlBr_3$, $AlF_3$) boron trifluoride, iron-(III)-halogenide, zinc halogenide, tin halogenide and titanium tetrachloride. Corresponding acetylacetonates may also be used for the isomerization of β-IPO and HIP at corresponding temperatures.

Active alkali- and earth alkali salts used as isomerization catalysts according to the invention are for example the alkali- or earth metal alcaline halogenide compounds of groups IB, IIB and VIIIB or corresponding Lewis acids known to the person skilled in the art. Examples of alkali- or earth metal alcaline halogenides are LiCl, NaCl, KCl, $MgCl_2$ $MgBr_2$, or $CaCl_2$.

Most preferably, the mixture obtained as an intermediate is isomerized in the presence of a solid, acid or super acid catalyst and the reaction proceeds as a solid/liquid two-phase process.

The quantity of catalyst in relation to the isomerizing substrate mixture β-IPO/HIP varies greatly depending on the type of catalyst used. In general very good yields can be achieved with adequate space-time yields when using $10^{-2}$ mol % to 1000 mol % preferably between $10^{-2}$ mol % to 50 mol % of catalyst. In principle, when using very acid isomerization catalysts (strong Brönstedt acids or super acids with Ho>−11.9), very low catalyst quantities of $10^{-2}$ mol % to 5 mol % are sufficient. When using Lewis acids, which are at least partially soluble in the reaction mixture, a catalyst concentration of $10^{-1}$ mol % to 5 mol % is normally sufficient and with heavy soluble salts catalyst concentrations are normally set at 1 mol % to 50 mol % to ensure adequate reaction times. When using heterogeneous catalysts, either the salt catalyst can be used in suspension or the process can be carried out by the fixed bed method.

In one embodiment of the process according to the invention, the β-isophorone epoxide formed is isolated directly after elimination of excess peroxide and peracid. On a laboratory scale it is also possible to shake with a little aqueous sodium bisulphite solution until the result of the peroxide test is negative. When working with excess β-IP, it is necessary to ensure, once the reaction is complete, that no excess peracid is left in the product mixture. Once the reaction is complete and peroxide impurities have been destroyed a product mixture remains which consists substantially of carboxylic acid, β-IPO, hydroxyisophorone and the solvent. The carboxylic acid can be separated off by fractionation and thus recycled. A further possibility for separating the organic carboxylic acid is extraction with a polar extracting agent, which is immiscible with the organic phase and inert towards the product. In the simplest case, the carboxylic acid formed can be extracted with a little water.

After separating off the carboxylic acid a mixture of β-IPO and HIP remains in the solvent of the epoxidation reaction, which can usefully also be used as a solvent for the subsequent isomerization. After isomerization the isomerization catalyst can be separated off by conventional separation processes such as distillation or extraction or simple centrifugation in the case of non-soluble, heterogeneous suspension catalysts.

Before isomerization, intermediate isolation of β-IPO may also be carried out by distillation, the solvent normally constituting the low-boiling component in relation to β-IPO. When using high-boiling absorbents, extracting agents or solvents such as the phosphoric acid triesters mentioned above, β-IPO can also be the volatile component. The remaining reaction medium can be fed back into the reaction after separation from the product.

After isomerization the DH-KIP obtained, which is normally dissolved in the organic solvent, can be isolated by suitable methods. A high degree of product purity is obtained by crystallization or distillation.

The purity of the dihydroketoisophorone isolated in this way corresponds to the product quality required for use as an educt for synthesis of trimethylhydroquinone (TMHQ) and trimethylhydroquinonediacetate (TMHQ-DA), the intermediates for synthesis of vitamin E acetate.

EXAMPLE 1

Reaction of β-isophorone with toluenic perpropionic acid

37 Gramm (g), (0.5 mol), propionic acid is placed in a 250 ml three neck flask at room temperature under nitrogen. 34 g of a 50 wt.-% hydrogen peroxide solution (i.e. 0.51 mol $H_2O_2$ and 0.94 mol water) and 15 g (0.15 mol) concentrated sulfuric acid are added simultaneously to the solution within 5 minutes with external cooling. The cooling and the corresponding rate of addition ensure that the temperature does not exceed 25° C. The molar quotient of $H_2O_2$: propionic acid: $H_2SO_4$ at this stoichiometry is 1.5:1.5:0.45. After the solution obtained has been stirred for 15 minutes at room temperature, the solution is extracted with 2×100 ml toluene, obtaining 230 g of a toluenic perpropionic acid which contains non-converted propionic acid and $H_2O_2$ as well as peracid and toluene. The toluenic solution of perpropionic acid which still contains $H_2O_2$ groups and non-converted propionic acid is transferred to a 500 ml three neck flask fitted with an internal thermometer, dropping funnel and gas bubble counter. 46 g β-IP (GC content: 99.5%; 0.33 mol) is dropped in within 20 minutes, under nitrogen., while keeping the solution at an internal temperature of 10° C. The mixture is left to react for 1 hour at 10° C. and for a further hour at room temperature. The toluenic product solution obtained is examined against an added internal standard (dodecane), the following results being obtained:

Converted β-IP: 21.51 g (47.2%)
Yield β-IPO: 21.28 g (41.8% of theoretical)
Selectivity β-IPO: 88.6% of theoretical
Selectivity alpha-IP: 0.11 g (0.52%)
Selectivity HIP: 0.91 g (3.8%)

The example demonstrates that when working with toluenic propionic acid, good β-IPO selectivities can be achieved while largely suppressing re-isomerization to alpha-IP and the consecutive reaction to HIP.

EXAMPLE 2

Reaction of β-isophorone with benzenic perpropionic acid 37 g (0.5 mol) propionic acid is placed in a 250 ml three neck flask at room temperature under nitrogen. First 15 g (0.15 mol) concentrated sulfuric acid and then 34 g of a 50 wt.-% hydrogen peroxide solution (0.51 mol $H_2O_2$ and 0.94 mol water) are added to the solution within 5 minutes with external cooling. The molar quotient of $H_2O_2$ : propionic acid: $H_2SO_4$ of the starting solution is 3:3:0.9 at this to stoichiometry (values in relation to the molar β-IP quantity to be oxidized).

External cooling with an ice bath ensures that the reaction temperature does not exceed 20° C. and stirring continues for a further 30 minutes. The solution thus obtained is extracted with 3×60 ml benzene. The extracted benzenic phase is dried with $MgSO_4$, a clear benzenic phase being obtained after filtration, which contains perpropionic acid, propionic acid and hydrogen peroxide. A total of 38 g of starting solution are converted to the organic phase by extraction with benzene.

The benzenic solution of perpropionic acid is transferred to a 500 ml three neck flask fitted with an internal thermometer, dropping funnel and gas bubble counter. 23 g β-IP (GC content: 99.5%; 0.166 mol) is dropped in within 10 minutes under nitrogen, while keeping the solution at an internal temperature of 20+ C. Stirring is continued for a further 90 minutes and the course of the reaction is monitored by GC. The results are given in Table 1.

TABLE 1

| Reaction Time [min] | % β-IP | % alpha-IP | % β-IPO | % HIP | % DH KIP |
|---|---|---|---|---|---|
| 0 | 99, 6 | 0 | 0 | 0 | 0 |
| 25 | 16, 3 | 1, 2 | 81, 4 | 0, 1 | 0 |
| 60 | 4, 1 | 1, 3 | 92, 4 | 0, 2 | 0 |

After 95 minutes the reaction is terminated, the benzenic product solution is cooled to room temperature and is washed with 10 wt.-% aqueous $NaHSO_3$ solution. The results of GC quantification of the product solution are as follows:

Converted β-IP: 22.25 g (97%)
Yield β-IPO: 23.8% (93% of theoretical)
Selectivity β-IPO: 95.9% of theoretical.
Selectivity alpha-IP: 0.03 g (0.14%)
Selectivity HIP: 0.32 g (1.3%)

The example demonstrates that, when working with benzenic propionic acid, very good β-IPO selectivities can be achieved while largely suppressing re-isomerization to alpha-IP and consecutive reaction to HIP.

COMPARATIVE EXAMPLE 1
Reaction of β-isophorone with 15 wt.-% aqueous peracetic acid 6.9 g (50 mmol) β-isophorone is placed in a three neck flask while stirring with the magnetic stirrer and 50 g (approx. 100 mmol) of a 15 wt.-% peracetic acid is dropped in slowly over a period of 20 minutes, in such a way that the internal temperature of the solution did not exceed 25° C. To begin with the solution has two phases, but during the reaction it becomes a homogeneous single phase. After 3 hours the reaction is terminated and the results are quantified by GC:

Converted β-IP: 6.83 g (99%)
Selectivity β-IPO: 0.23 g (3.0% of theoretical)
Selectivity alpha-IP: 0.35 g (4.6%)
Selectivity HIP: 3.08 g (40.4%)

The corresponding β-IP diol is also detected with a selectivity of 8% as well as other non-characterized products. Overall, the reaction is non-selective and is not very suitable for the selective production of β-IP epoxide.

EXAMPLE 3
Production of Dihydroketoisophorone 74 g (1 mol) propionic acid is placed in a 250 ml three neck flask at room temperature under nitrogen. First 61 g (0.62 mol) concentrated sulfuric acid and then 68 g of a 50 wt.-% hydrogen peroxide solution (1 mol $H_2O_2$ and 1.88 mol water) are added to the solution within 10 minutes with external cooling. The molar quotient of $H_2O_2$ : propionic acid: $H_2SO_4$ of the starting solution is 1:1:0.62 at this stoichiometry. External cooling with an ice bath ensures that the reaction temperature does not exceed 20° C. and stirring continues for a further 30 minutes. The solution thus obtained is extracted with 1×80 g and then with 3×30 g toluene. The extracted toluenic phase is dried with $MgSO_4$, a clear toluenic phase being obtained after filtration, which contains perpropionic acid (19.2 wt.-%), propionic acid (9.1 wt.-%), hydrogen peroxide (0.15 wt.-%) and water (0.3 wt.-%).

49.9 g β-IP (GC content: 97.4%; 0.355 mol) is transferred to a 250 ml three neck flask fitted with an internal thermometer, dropping funnel and gas bubble counter. Half of the toluenic solution of the perpropionic acid is dropped in within 15 minutes under nitrogen, while keeping the internal temperature of the solution at 15° C. Stirring is continued for a further 120 minutes at 30° C. and the course of the reaction is monitored by GC. The toluenic product solution is then cooled to room temperature and washed with a little 10 wt.-% aqueous $NaHSO_3$ solution; a Merck peroxide test is carried out to ensure that no peracid remains.

The following result is obtained from GC quantification of the product solution:

Yield β-IPO: 82.8%
Yield HIP: 7.5%
Yield DH-KIP: 1%

Selectivity (β-IPO+HIP+DH-KIP)=94%

After drying with $MgSO_4$ the solution is filtered. The toluenic solution of β-IPO (0.35 mol) and 0.32 g (0.5 mol %) $MgBr_2$ were placed in a 500 ml three neck flask fitted with an internal thermometer, Liebig cooler and mechanical stirrer, at room temperature under nitrogen. The solution was heated at 85° C. while stirring. After a reaction time of 45 minutes, the following results are obtained from GC quantitative analysis:

Converted β-IPO: 100%
Yield DH-KIP: 97%
Selectivity β IPO in relation to (DH-KIP+HIP): 98.6%

1.6% HIP remains in the product solution.

EXAMPLE 4–7
Production of DH-KIP with $MgBr_2$ (1 mol % in relation to the total of isomerisable intermediates) as catalyst at various temperatures 20 ml of a toluenic solution of β-IPO (produced as in Example 3; 0.02 mol β-IPO) are placed in a Schlenck tube with 1 mol % $MgBr_2$. Three identical educt solutions are prepared to examine the effect of temperature on the speed and selectivity of isomerization. The solutions are heated at different temperatures (50° C., 70° C. and 90° C.) Each test lasted for 60 minutes. In example 7, air (or atmospheric oxygen) was excluded by suitable manipulation of the solutions under nitrogen. The results are shown in Table 2.

TABLE 2

| Test | Cond.: Time./ Temp. | % β-IPO | % HIP | % DH KIP |
|---|---|---|---|---|
| Example 4 | 60 min at 50° C. | 33 | 4 | 59 |
| Example 5 | 60 min at 70° C. | 2 | 12 | 79 |
| Example 6 | 60 min at 90° C. | 0 | 0 | 91 |
| Example 7 | 60 min at 90° C. (nitrogen) | 0 | 0 | 95 |

EXAMPLE 8–10
Reaction of β-IPO with $MgBr_2$ at various catalyst concentrations 20 ml of a toluenic solution of β-IPO (produced as in Example 3; 0.02 mol β-IPO) is placed in a Schlenck tube with $MgBr_2$. Three identical educt solutions were prepared to examine the effect of catalyst concentration on the speed and selectivity of isomerization. The solutions were heated at 85° C. at differing catalyst concentrations. Each test lasted for 45 minutes. The results are shown in Table 3.

TABLE 3

| Test | Catalyst [mol %] | % β IPO | % HIP | % DH KIP |
|---|---|---|---|---|
| Example 8 | $MgBr_2$ [1 mol %] | 0 | 0 | 92 |
| Example 9 | $MgBr_2$ [0.5 mol %] | 0 | 0 | 92 |
| Example 10 | $MgBr_2$ [0.1 mol %] | 0 | 29 | 33 |

EXAMPLE 11–12
Reaction of β-IPO with toluenesulfonic acid as catalyst

Two x 20 ml of a toluenic solution of β-IPO [produced as in Example 3; 0.02 mol (β-IPO+HIP)- content] are placed in a Schlenck tube with 1 mol % p-toluenesulfonic acid.

The solutions were heated at different temperatures (50° C., 100° C.). Each test lasted for 60 minutes:

Ex. 11: T=100° C. Converted β-IPO (after 16 hours): 100%
Yield DH-KIP: 79%
Selectivity (DH-KIP+HIP): 84%

Ex. 12: T=50° C. Converted β-IPO (after 24 hours): 100%
Yield DH-KIP: 52%
Selectivity (DH-KIP+HIP): 55%

EXAMPLE 13
Reaction of β-IPO with $CaCl_2$ 74 g (1 mol) propionic acid is placed in a 250 ml three neck flask at room temperature under nitrogen. First 61 g (0.62 mol) concentrated sulfuric acid and then 68 g of a 50 wt.-% hydrogen peroxide solution (1 mol $H_2O_2$ and 1.88 mol water) are added to the solution within 10 minutes with external cooling. The molar quotient of $H_2O_2$: propionic acid: $H_2SO_4$ of the starting solution is 1:1:0.62 at this stoichiometry. External cooling with an ice bath ensures that the reaction temperature does not exceed 20° C. and stirring continues for a further 30 minutes. The solution thus obtained is extracted with 1×80 g+3 ×40 g toluene. The extracted toluenic phase is dried with $MgSO_4$, a clear toluenic phase being obtained after filtration, which contains perpropionic acid (17 wt.-%), propionic acid (8.1 wt.-%), hydrogen peroxide (0.22 wt.-%) and water (0.3 wt.-%).

14.9 g β-IP (GC content: 97.4%; 0.106 mol) were transferred to a 250 ml three neck flask fitted with an internal thermometer, dropping funnel and gas bubble counter. 62.5 g (0.117 mol) of the toluenic solution of perpropionic acid is dropped in within 15 minutes under nitrogen, while keeping the internal temperature of the solution at 15° C. Stirring is continued for a further 120 minutes at 30° C. and the reaction is monitored by GC.

The toluenic product solution is washed with a little 10 wt.-% aqueous $NaHS_3$ solution. The results of GC quantification of the product solution are as follows: β-IPO 85%, HIP 6% and DH-KIP 1%. After drying with $MgSO_4$ the solution was filtered.

The toluenic solution of β-IPO (0.1 mol) and 0.22 g (2 mol %) $CaCl_2$ are placed in a 100 ml three neck flask fitted with an internal thermometer, Liebig cooler and mechanical stirrer, under nitrogen. The solution was heated at 100° C. for 90 minutes. After terminating the reaction, the following results are obtained:

Converted β-IPO: 100%
Yield DH-KIP: 97.7%

EXAMPLE 14–20 AND COMPARATIVE EXAMPLE 2
Production of DH-KIP with various catalysts 74 g (1 mol) propionic acid is placed in a 250 ml three neck flask at room temperature under nitrogen. First 61 g (0.62 mol) concentrated sulfuric acid and then 68 g of a 50 wt.-% hydrogen peroxide solution (1 mol $H_2O_2$ and 1.88 mol water) are added to the solution within 10 minutes with external cooling. The molar quotient of $H_2O_2$: propionic acid: $H_2SO_4$ of the starting solution is 1:1:0.62 at this stoichiometry.

External cooling with an ice bath ensures that the reaction temperature does not exceed 20° C. and stirring continues for a further 30 minutes. The solution thus obtained is extracted with 80+3*30 g toluene. The extracted toluenic phase is dried with $MgSO_4$, a clear toluenic phase being obtained after filtration, which contains perpropionic acid (19.2 wt.-%), propionic acid (9.1 wt.-%), hydrogen peroxide (0.16 wt.-%) and water (0.25 wt.-%).

14.9 g β-IP (GC content: 97.4%; 0.106 mol) were transferred to a 250 ml three neck flask fitted with an internal thermometer, dropping funnel and gas bubble counter. 62.5 g (0.117 mol) of the toluenic solution of perpropionic acid is dropped in within 15 minutes under nitrogen, while keeping the internal temperature of the solution at 15° C. Stirring is continued for a further 120 minutes at 30° C. and the course of the reaction is monitored by GC. After 125 minutes the reaction is terminated and the toluenic product solution is cooled to room temperature and washed with a little 10 wt.-% aqueous $NaHSO_3$ solution. The reaction is exothermic and the temperature is maintained at 15 to 25° C. by external cooling. After drying with $MgSO_4$ the solution as filtered.

19 g (0.1 mol) of the toluenic solution of β-IPO together with the corresponding catalyst salt is placed in a 100 ml Sclenck tube at room temperature under nitrogen. The solution is then heated at 100° C. The solution remains at 100° C. for 120 minutes. The results of GC quantification of the product solution are as follows in Table 4.

TABLE 4

| Test | Catalyst | mol % | T (° C.) | Time (min) | Yield % | Selectivity % |
|---|---|---|---|---|---|---|
| Ex. 14 | LiCl | 5 | 100 | 120 | 100 | 100 |
| Ex. 15 | LiCl | 1 | 100 | 120 | 91 | 100 |
| Ex. 16 | NaCl | 5 | 100 | 120 | 100 | 98 |
| Ex. 17 | KCl | 5 | 100 | 120 | 100 | 97 |
| Ex. 18 | LiBr | 5 | 100 | 120 | 100 | 100 |
| Ex. 19 | $TiO_2$ | 5 | 100 | 120 | 54 | 89 |
| Ex. 20 | $MgCl_2$ | 5 | 100 | 120 | 97 | 100 |
| Comparative Example 2 | None | / | 100 | 120 | 42 | 89 |

EXAMPLE 21
Reaction of β-IPO with $FeCl_3$ 20 ml (5 mol %) of the toluenic solution of β-IPO and $FeCl_3$ is placed in a Schlenck tube under nitrogen. The solution was heated at 100° C. The reaction time is 80 minutes. The following results are obtained from quantitative GC analysis:

Yield DH-KIP: 86.4%
Selectivity DH-KIP: 93%

EXAMPLE 22
Reaction of β-IPO with $AlF_3$ 20 ml (5 mol %) benzenic solution of β-IPO and $AlF_3$ is placed in a Schlenck tube under nitrogen. The solution is heated at 100° C. The reaction time was 80 minutes. The following results are obtained from quantitative GC analysis:

Yield DH-KIP: 63.9%
Selectivity DH-KIP: 74%

EXAMPLE 23
Production of DH-KIP from β-IP 74 g (1 mol) propionic acid is placed in a 250 ml three neck flask at room temperature under nitrogen. First 61 g (0.62 mol) concentrated sulfuric acid and then 68 g of a 50 wt.-% hydrogen peroxide solution (1 mol $H_2O_2$ and 1.88 mol water) are added to the solution within 10 minutes with external cooling. The molar quotient of $H_2O_2$: propionic acid: $H_2SO_4$ of the starting solution is 1:1:0.62 at this stoichiometry. External cooling with an ice bath ensures that the reaction temperature does not exceed 20° C. and stirring continues for a further 30 minutes. The solution thus obtained is extracted with 1×80 g and 3×30 g toluene. The extracted toluenic phase is dried with $MgSO_4$, a clear toluenic phase being obtained after filtration which contains perpropionic acid (19.2 wt.-%), propionic acid (9.1 wt.-%), hydrogen peroxide (0.16 wt.-%) and water (0.25 wt.-%).

The toluenic solution of perpropinic acid (0.445 mol) is transferred to a 500 ml three neck flask fitted with an internal thermometer, dropping funnel and gas bubble counter. 49.2 g β-IP (GC content: 97.4%; 0.356 mol) is dropped in within 15 minutes under nitrogen, while keeping the internal temperature of the solution at 30° C. (β-IP/peracid=0.8 1). Stirring is continued for a further 100 minutes at 30° C. and the course of the reaction is monitored by GC. After 105 minutes the reaction is terminated and the toluenic product solution is cooled to room temperature and washed with a little 10 wt.-% aqueous $NaHSO_3$ solution. After drying with $MgSO_4$ the solution was filtered.

The toluenic solution of β-IPO/HIP (0.35 mol) and 0.33 g (0.5 mol %) $MgBr_2$ were placed at room temperature, under nitrogen, in a three neck flask fitted with an internal thermometer, Liebig cooler and mechanical stirrer. The solution is heated for 30 minutes to 80° C. The results of GC quantification of the product solution are as follows:

Converted β-IPO: 100%

Yield DH-KIP: 97%

Selectivity (HIP+DH-KIP) 98%

Further variations and modifications of the foregoing will be apparent to those skilled in the art and are intended to be encompassed by the claims appended hereto.

German priority application 100 24 264.2 is relied on and incorporated herein by reference.

We claim:

1. A process for the production of an intermediate mixture of the β-isophorone epoxide represented by the structure:

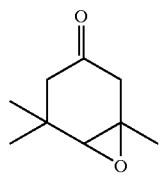

and its isomer-4-hydroxyisophorone (HIP),

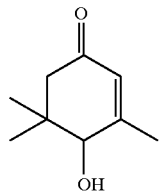

comprising reacting β-isophorone (3,5,5-trimethylcyclohex 3-en-1-one) represented by the structure

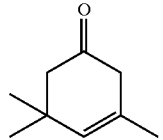

with an organic percarboxylic acid in the form of its non-aqueous solution in an inert organic solvent at a temperature of 0° C. to 300° C., the percarboxylic acid used as oxidizing agent being formed in a pre-determined equilibrium and absorbed or extracted with the solvent used for oxidation, to thereby obtain an intermediate mixture.

2. The process according to claim 1, further comprising isomerizing said intermediate mixture "in situ" thermally or in the presence of an acid catalyst or in the presence of a salt.

3. The process according to claim 2, wherein isomerizing said mixture of β-IPO and HIP obtained as an intermediate is carried out in an organic solvent, which was also used for extraction of the organic percarboxylic acid.

4. The process according to claim 3, wherein the isomerizing is carried out thermally in a temperature range of 20° C. to 200° C.

5. The process according to claim 4, wherein a protonic acid with a pKA<3 is said acid catalyst for isomerization.

* * * * *